United States Patent
Radow

Patent Number: 6,090,060
Date of Patent: Jul. 18, 2000

[54] ADJUSTABLE PRESSURE EYE PATCH

[76] Inventor: Brett K. Radow, 6621 Kanahwa Ave. SE., Charleston, W. Va. 35304

[21] Appl. No.: 09/036,508

[22] Filed: Mar. 6, 1998

Related U.S. Application Data

[62] Division of application No. 08/609,509, Mar. 1, 1996, Pat. No. 5,769,806.

[51] Int. Cl.[7] ............................ A61F 13/12; A61F 13/00; A61F 9/00
[52] U.S. Cl. ............................ 602/74; 602/41; 128/858
[58] Field of Search ................ 602/41, 54, 57–59, 602/74, 79; 128/858, 892, 893, 888; 2/15; 607/108, 109, 114

[56] References Cited

U.S. PATENT DOCUMENTS

| | | | |
|---|---|---|---|
| 2,573,791 | 11/1951 | Howells | 602/14 |
| 3,952,735 | 4/1976 | Wirtschafter et al. | 602/74 |
| 4,134,401 | 1/1979 | Galician | 602/74 |
| 4,793,003 | 12/1988 | Riedel et al. | 602/74 X |
| 4,862,902 | 9/1989 | Goffman | 128/858 |
| 4,907,580 | 3/1990 | Leonardi | 602/74 |
| 4,951,658 | 8/1990 | Morgan et al. | 602/74 |
| 5,086,763 | 2/1992 | Hathman | 602/42 |
| 5,431,622 | 7/1995 | Pyrozyk et al. | 602/2 |
| 5,628,772 | 5/1997 | Russell | 607/119 |
| 5,769,806 | 6/1998 | Radow | 602/41 |
| 5,887,590 | 3/1999 | Price | 602/54 X |

Primary Examiner—Richard J. Apley
Assistant Examiner—Denise Pothier
Attorney, Agent, or Firm—Robert N. Blackmon

[57] ABSTRACT

Disclosed is a pressure eye patch in which an inner membrane is positioned over the patient's eye and fixed thereto by means of adhesive on its inner side with an outer membrane which is superimposed over the inner membrane, thus forming a cavity that is interposed between the outer membrane and the inner membrane. There is an elongated longitudinal slit in the outer membrane which allows the outer membrane to be opened to allow access to the cavity. Cushioning material such as sterile gauze may be inserted into the cavity through this opening. Alternatively, a cooling or heating material may also be emplaced in the cavity. Instead of the elongated slit there may be a partial peripheral opening between the front and rear membranes to allow access to the cavity.

10 Claims, 2 Drawing Sheets

ADJUSTABLE PRESSURE EYE PATCH

This application is a division of application Ser. No. 08/609,509, filed Mar. 1, 1996, now U.S. Pat. No. 5,769,806.

BACKGROUND OF THE INVENTION

1. Field of the Invention

The present invention relates to bandages and more particularly to eye patches.

2. Brief Description of the Prior Art

Pressure patching has long been a technique and treatment used for aid in healing an injury and for use after surgery to the eye.

The patch immobilizes the eyelid which prevents reinjury to the damaged area. Pressure patching is indicated in any abrasion to the cornea. Pressure patching is also used after cataract surgery as well as in other anterior segment surgeries.

Various eye pressure patches are disclosed in the prior art. U.S. Pat. No. 3,908,645, for example, discloses a patch in which a resilient pad which has an inner layer of absorbent non-woven web material attached to a foam layer and a nonadherent facing bonded to the web material to prevent sticking of the pad to the tissue when the bandage is in use.

A disadvantage of the pressure patches of the prior art, however, exists in that adjustments in pressure are not possible without reconstructing the entire patch. Also, no prior art exists for a means of adjustment in the temperature environment of the eye by means of an eye patch.

A need, therefore, exists for an eye pressure patch in which different pressure and temperature conditions may be easily obtained and in which one type of dressing may be easily replaced with another.

SUMMARY OF THE INVENTION

The pressure eye patch of the present invention comprises a single integral bandage which could be sterile or non-sterile, in which an inner membrane is positioned over the patient's eye and fixed thereto by means of adhesive on its inner side, with an outer membrane that is superimposed over the inner membrane, thus forming a convex shaped cavity which is interposed between the outer membrane and the inner membrane. There is an elongated longitudinal slot in the outer membrane which allows the outer membrane to be opened to allow access to the cavity. Cushioning material such as sterile gauze may be inserted into the cavity through this opening, and the amount of pressure applied may be varied by the amount of material used. Alternatively, a cooling material may be inserted into the cavity. Still another alternative would be to insert a heating material into the cavity. An elongated flap is positioned adjacent the elongated slot and closes the slit by being fixed to the outer membrane by means of an adhesive layer on the inner side of the flap.

Together the inner membrane and the outer membrane comprise one unit bandage. This bandage, therefore, essentially has two distinct, but structurally well-attached layers, which form between them an inner pocket or cavity for further utilization and increased efficiency of the bandage. The use of this cavity is specifically directed towards the goals of healing corneal defects, corneal injury, other anterior segment injuries, corneal erosions and other inflammations, irritations and diseases of the anterior segment of the eye, as well as following surgeries to the anterior and posterior segments of the human eye.

By manipulation of the area between the inner and outer layers of this bandage, known means of healing can be instituted combined with other healing mechanisms described herein. These means can be applied directly to the wound and its surrounding tissue with ease by either patient or his care giver and remain in place for hours or longer without maintenance.

The bandage of the present invention, will be of less total weight than bandages commonly used, for example, after cataract surgery, thus reducing some discomfort likely to be experienced by the patient. The height of the bandage will also be reduced, thereby allowing the patient the use of his spectacles and increasing comfort during the recovery period.

The adhesive along the elongated flap or in the other embodiments, along the top side seal, will be protected by a thin paper or membrane material which can be removed when activation of the sealing adhesive is necessary, after the introduction of the selected pocket material. Furthermore, the bandage of the present invention may be used without addition of other materials if the desired or adequate pressure is obtained without it.

The adjustment of the pressure applied to the eye to immobilize the eyelids, or to deliver other healing means, can be individually tailored for the particular patient. Patients with deeper set eyes, or prominent facial features, such as their cheek bones, nose or forehead will usually require extra batting for adequate pressure patching while those with the opposite characteristics may not. Several pressure settings can be obtained on the same individual through variations of the cavity material.

The cooling materials which may be used with this eye patch will be either urea crystals activated with water, blue ice by GOTT, or water which can be frozen in self-contained packets, which will easily be introduced into the pocket. This unique cold compress, which self adheres, can then be placed over the necessary eye or other localized tissue to reduce swelling and relieve the pain of inflamed tissue. The known mechanism of action of the cooling material is due in part to a vasoconstrictor property. If the blood supply to an injured area is reduced through vasoconstriction, then less swelling will occur and further tissue damage from edema can be limited. Cold compresses within twenty-four hours of injury are known to be vastly beneficial in the healing process.

The heating process, as suggested for use with this bandage, is supplied by either magnesium sulfate crystals activated by water or through other known materials which are individually packaged to fit this bandage and release heat by a controlled mechanism. The use of such materials would be indicated when increased vascularization is needed. This mechanism of action is known as vasodilation. In certain instances an increased blood flow would be beneficial in the healing process. An example, which would demonstrate the use of this bandage as a warm compress, would be in the treatment of styes, chalazions and other cysts of the eyelids or surrounding tissue. The use of warm compresses in these situations is well known. The use of heat increases blood flow, which in itself delivers the naturally occurring antibiotics within the blood stream to the injured or inflamed area. In addition to this effect, the warmth allows access of applied medicines to be more readily absorbed, and therefore closer in proximity to the infected area. Also, vasodilation by heat will allow further advanced profusion of the prescribed medicines to the interstitial cellular area.

BRIEF DESCRIPTION OF THE DRAWINGS

The pressure eye patch of the present invention is further described with reference to the accompanying drawings in which.

DETAILED DESCRIPTION OF THE PREFERRED EMBODIMENTS

Figure 1:
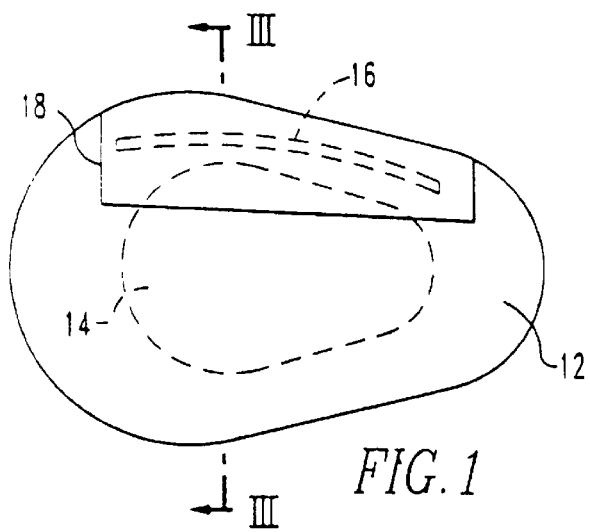
FIG. 1 is a front plan view of a preferred embodiment of the pressure eye patch of the present invention.
Figure 3:
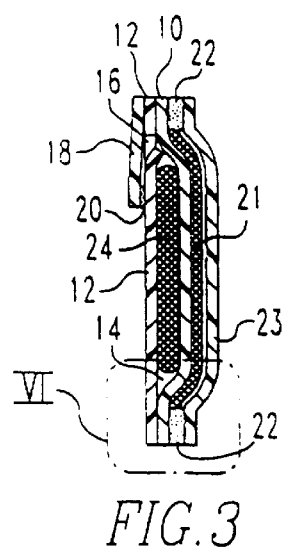
FIG. 3 is a cross sectional view of the eye patch through III—III in FIG. 1.
Figure 2:
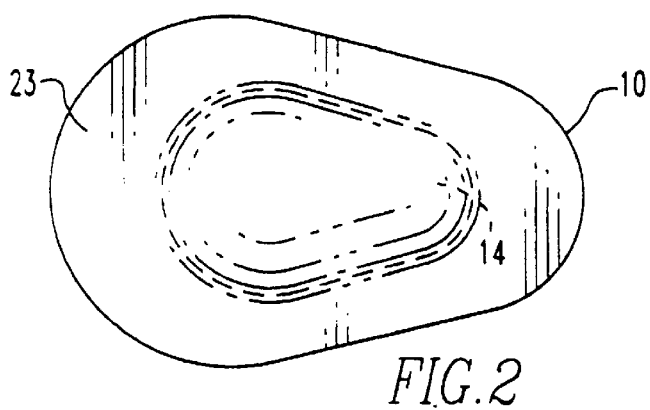
FIG. 2 is a back plan view of the pressure eye patch shown in FIG. 1.
Figure 6:
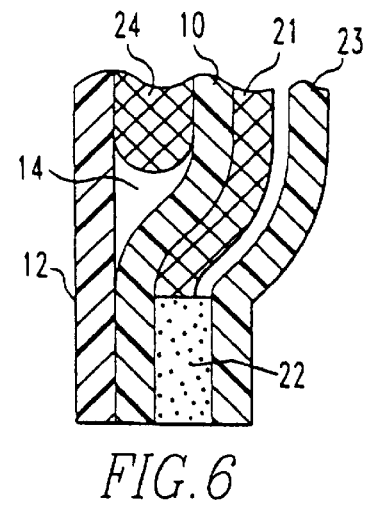
FIG. 6 is a detailed enlarged view of area VI in FIG. 3.
Figure 4:
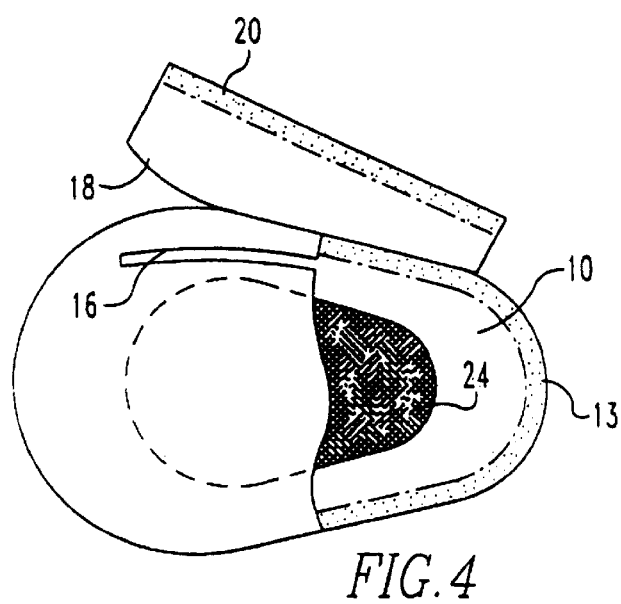
FIG. 4 is a cut away view of the eye patch shown in FIG. 1.
Figure 5:
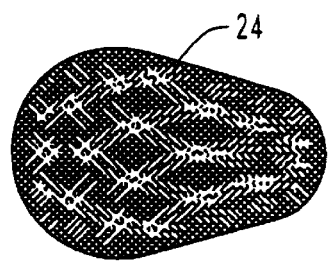
FIG. 5 is a full front plan view of the gauze element shown in place in FIG. 4.

Referring to FIGS. 1–5, the eye patch comprises a single bandage which is an integral combination of an inner membrane 10, and an outer membrane 12 in which the outer membrane is superimposed over and fixed to said inner membrane by a peripheral and intermediate adhesive layer 13. As used herein, the term "inner" means the part of the eye patch which would be positioned against the patient's eyelid in normal use. The term "outer" means the part of the eye patch which would ordinarily be positioned on the opposite side of the patch. The inner and outer membranes will preferably be flexible polymeric material or other such material well known in the art for the construction of bandages. A convex shaped cavity 14 is interposed between the outer membrane and inner membrane. The opening in the outer membrane is an elongated longitudinal slit 16. An elongated flap 18 is longitudinally positioned adjacent to the elongated slit, and an adhesive fastening surface 20 is provided to fix the elongated flap to the outer membrane so that the opening in the membrane is closed when the elongated flap is fixed to the membrane. On the inner side of the inner membrane, there is a sterile gauze pad 21. Surrounding the gauze pad 21 there is a peripheral adhesive surface 22 covered by a paper guard 23 which may be used to fix the patch to the skin adjacent the eye so that the eye patch may be placed over the eye to be treated. The cavity may be filled with a cushioning material such as sterile gauze which may be in the form of a preformed pillow-shaped element 24. This pillow-shaped element causes the bandage to bulge convexly toward the patient's eye to place pressure on the eye. Such pressure may be varied by changing the size or shape of this pillow-shaped element. Consequently, the patch may be used with any one of a variety of differently sized pillow-shaped elements. Alternately, a temperature influencing cooling material or a heating material may be positioned in the cavity. This might preferably be contained within a pillow-shaped element similar in size and shape to element 24.

Figure 7:
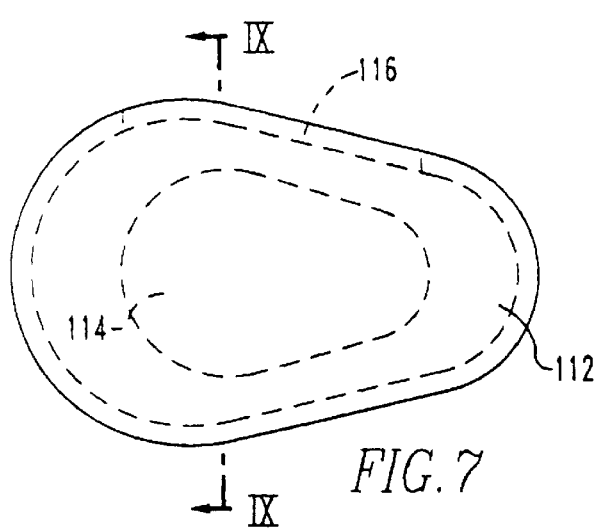
FIG. 7 is a front plan view of an eye patch representing an alternate embodiment of the present invention.
Figure 9:
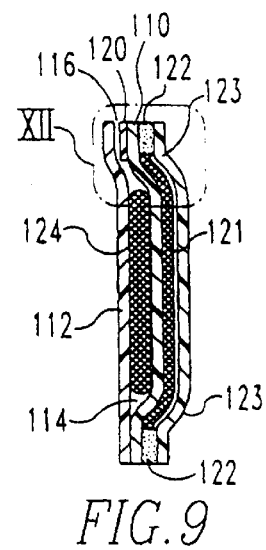
FIG. 9 is a cross sectional view of the eye patch through IX—IX in FIG. 7.
Figure 8:
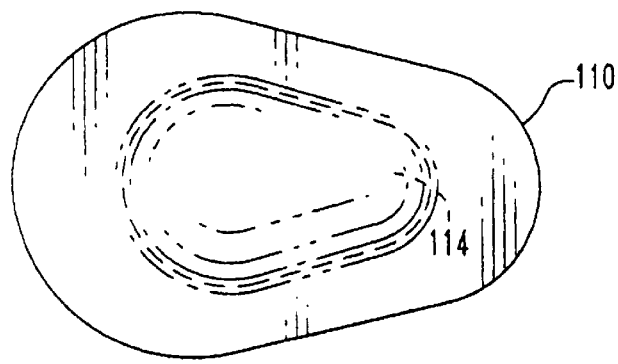
FIG. 8 as a back plan view of the eye patch shown in FIG. 7.
Figure 12:
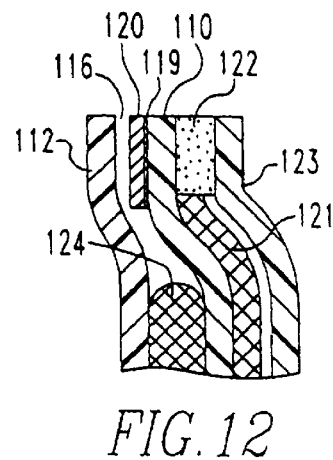
FIG. 12 is a detailed enlarged view of area XII in FIG. 9.
Figure 10:
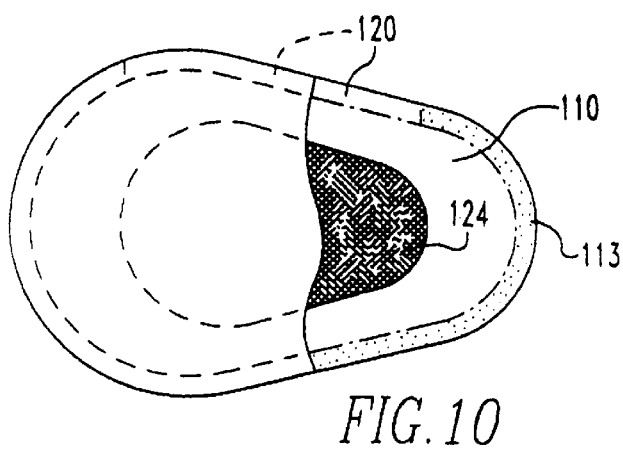
FIG. 10 is a cut away view of the eye patch shown in FIG. 7.
Figure 11:
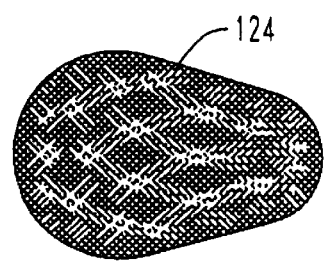
FIG. 11 is a full front plan view of the gauze element shown in place in FIG. 10.

Referring to FIGS. 7–11, the second embodiment of the eye patch, like the first embodiment, comprises a single bandage which is an integral combination of an inner membrane 110 and an outer membrane 112 in which the outer membrane is superimposed over the inner membrane, and is fixed to it by an intermediate peripheral adhesive layer 113. A convex shaped cavity 114 is interposed between the outer membrane and the inner membrane. The tops of the two membranes are not initially fixed together since the peripheral adhesive layers as at 119 are covered by paper guards as at 120 so that an opening 116 is formed to allow access to the cavity. After the cavity has been filled, as is described below, this opening may be closed by removal of the paper guards to allow the peripheral adhesive surfaces to be attached to each other and to thereby close the cavity. On the inner side of the inner membrane, there is a sterile gauze pad 121. Surrounding this gauze pad 121 there is a peripheral adhesive surface 122 covered by a paper guard 123 which may be used, after removal of the guard, to fix the patch to the skin adjacent the eye in a position so that the patch is superimposed over the eye to be treated. The cavity may be filled with a cushioning material such as sterile gauze which may be in the form of a preformed pillow-like element 124. This pillow-like element causes the bandage to bulge convexly toward the patient's eye to place pressure on the eye. Such pressure may be varied by changing the size or shape of this pillow-like element. Alternately, a heating or cooling material may be used in the cavity. This heating or cooling element contained in a pillow-shaped element may be of the same general size and shape as element 124 shown in FIG. 11.

Although the invention has been disclosed with some particularity, it is to be understood that the present disclosure is only an example and the scope of the invention is defined by the following claims.

What is claimed is:

1. A method for adjusting pressure on an eye of a patient comprising the steps of:

(a) positioning over the eye a patch comprising an outer membrane superimposed over an inner membrane, a cavity interposed between said outer membrane and said inner membrane, and a peripheral opening between said inner and outer membranes to allow for the insertion and removal of a cushioning means in order to adjust pressure on the eye; and (b) emplacing said cushioning means in said cavity, whereby the pressure applied to the eye may be adjusted by selecting said cushioning means from a variety of differently shaped and sized cushioning means.

2. The method of claim 1 wherein the cushioning means causes the eye patch to bulge convexly inwardly toward the eye.

3. The method of claim 1 wherein a fastening means is provided to close said peripheral opening between the inner and outer membranes.

4. The method of claim 1 wherein there are fastening means on the inner membrane to fix the eye patch in a position superimposed over the eye of the patient.

5. The method of claim 1 wherein the fastening means on the inner membrane is an adhesive.

6. The method of claim 1 wherein the cushioning means is a pad.

7. The method of claim 1 wherein the cushioning means is a gauze material.

8. The method of claim 1 wherein a cooling means is emplaced in the cavity.

9. The method of claim 1 wherein a heating means is emplaced in the cavity.

10. The method of claim 1 wherein the patch is a single integral bandage.

* * * * *